(12) United States Patent
Seeboth et al.

(10) Patent No.: US 9,073,872 B2
(45) Date of Patent: Jul. 7, 2015

(54) MOLECULES HAVING COMBINABLE GROUPS

(75) Inventors: Nicolas Seeboth, Clermont-Ferrand (FR); Serguey Ivanov, Orekhovo-Zouevo (RU); Jean-Luc Couturier, Lyons (FR); Manuel Hidalgo, Brignais (FR)

(73) Assignee: ARKEMA FRANCE, Colombes (FR)

( * ) Notice: Subject to any disclaimer, the term of this patent is extended or adjusted under 35 U.S.C. 154(b) by 69 days.

(21) Appl. No.: 13/809,767

(22) PCT Filed: Jul. 12, 2011

(86) PCT No.: PCT/FR2011/051652
§ 371 (c)(1),
(2), (4) Date: Mar. 4, 2013

(87) PCT Pub. No.: WO2012/007685
PCT Pub. Date: Jan. 19, 2012

(65) Prior Publication Data
US 2013/0211057 A1   Aug. 15, 2013

(30) Foreign Application Priority Data

Jul. 13, 2010  (FR) .................................... 10 55718

(51) Int. Cl.
*C07D 233/32* (2006.01)
*C07D 233/36* (2006.01)
*C07D 403/12* (2006.01)

(52) U.S. Cl.
CPC ............ *C07D 233/36* (2013.01); *C07D 233/32* (2013.01); *C07D 403/12* (2013.01)

(58) Field of Classification Search
CPC ..................................................... C07D 233/32
USPC ......................................................... 548/324.1
See application file for complete search history.

(56) References Cited

U.S. PATENT DOCUMENTS

| | | | |
|---|---|---|---|
| 7,186,845 B2 | 3/2007 | Fukushima et al. | |
| 2004/0010090 A1 | 1/2004 | Chino et al. | |
| 2011/0183098 A1 | 7/2011 | Hidalgo et al. | |

FOREIGN PATENT DOCUMENTS

| | | |
|---|---|---|
| WO | WO 2010/031956 | 3/2010 |
| WO | WO 2012/007684 | 1/2012 |

OTHER PUBLICATIONS

Thielepape et al. (CAPLUS Abstract of: [Abteilung] B: Abhandlungen (1922), 55B, 2929-39).*
Ikeda (CAPLUS Abstract of: US 3190878).*
Merli et al. (CAPLUS Abstract of: DE 1944745).*
Adcock et al. (CAPLUS Abstract of: DE 2118553).*
International Search Report for International Application No. PCT/FR2011/051652 mailed Oct. 19, 2011.
International Search Report for International Application No. PCT/FR2011/051651 mailed Oct. 25, 2011.

* cited by examiner

*Primary Examiner* — Robert Havlin
(74) *Attorney, Agent, or Firm* — RatnerPrestia

(57) ABSTRACT

The present invention relates to nitrogenous associative molecules comprising at least one unit rendering them capable of associating with one another or with a filler by noncovalent bonds, and comprising a function capable of reacting with a polymer containing unsaturations so as to form a covalent bond with said polymer.

5 Claims, No Drawings

MOLECULES HAVING COMBINABLE GROUPS

CROSS REFERENCE TO RELATED APPLICATIONS

This application is the U.S. National Phase application of PCT International Application No. PCT/FR2011/051652, filed Jul. 12, 2011, and claims priority to French Patent Application No. 1055718, filed Jul. 13, 2010, the disclosures of which are incorporated by reference in their entirety for all purposes.

FIELD OF THE INVENTION

The present invention relates to nitrogenous associative molecules comprising at least one unit rendering them capable of associating with one another or with a filler, via noncovalent bonds, and comprising a function capable of reacting with a polymer containing unsaturations so as to form a covalent bond with said polymer.

The modified polymers comprising associative groups along the polymeric chain are polymers comprising at least one unit rendering them capable of associating with one another or with a filler via noncovalent bonds. An advantage of these polymers is that these physical bonds are reversible under the influence of external factors, such as temperature or stress time, for example. Thus, the mechanical properties of these modified polymers can be modulated according to the parameters of the environment in which they are used.

Such polymers are, for example, described in the document published under number WO 2010/031956.

SUMMARY OF THE INVENTION

This document describes elastomers comprising flexible polymer chains associated with one another, firstly, via permanent crosslinking bridges having covalent bonds and, secondly, via crosslinking bridges having noncovalent bonds. The molecules grafted on to the elastomers comprise associative groups based on a nitrogenous heterocycle enabling the establishment of physical bonds. Mentioned among the associative groups envisioned in this document are imidazolidinyl, triazolyl, triazinyl, bis-ureyl and ureidopyrimidyl groups.

In order to modify the elastomers, said elastomer can be reacted with a molecule comprising, firstly, the associative group and, secondly, a reactive group forming a covalent bond with a reactive function borne by the elastomer. This therefore involves prior functionalization of the elastomer.

It is found, in addition, that the elastomers thus modified comprise a certain proportion of functions which have not reacted and which influence the final properties of the material.

This is the reason why research has been carried out on other processes for modifying polymers in order to introduce associative groups along the chain.

The objective of the present invention is therefore to propose an alternative for modification of polymers applicable also to polymers which do not comprise reactive functions.

This objective is achieved in that the inventors have just discovered novel molecules comprising both at least one associative group and at least one reactive group, which make it possible to modify a polymer, comprising at least one double bond, without it being necessary for the polymer in question to comprise reactive functions.

DETAILED DESCRIPTION

A subject of the invention is a compound comprising at least one group Q, and at least one group A linked together by at least and preferably one "spacer" group Sp, in which:
  Q comprises an azodicarbonyl unit,
  A comprises an associative group comprising at least one nitrogen atom,
  Sp is an atom or a group of atoms forming a link between Q and A.

A polymer grafted with a compound as defined above is mixed with fillers; said compound establishes only labile bonds with the fillers, which makes it possible to provide good polymer-filler interaction, beneficial for the final properties of the polymer, but without the drawbacks that too strong a polymer-filler interaction could cause.

The term "associative group" is intended to mean groups capable of associating with one another via hydrogen, ionic and/or hydrophobic bonds. According to one preferred embodiment of the invention, they are groups capable of associating via hydrogen bonds.

When the associative groups are capable of associating via hydrogen bonds, each associative group comprises at least one donor "site" and one acceptor site with respect to the hydrogen bond such that two identical associative groups are self-complementary and can associate together by forming at least two hydrogen bonds.

The compounds according to the invention comprising a group Q, a "spacer" group and an associative group can, for example, be represented by formula (Ia) below:

A-Sp-Q                    (Ia).

The compounds according to the invention comprising a group Q, a "spacer" group and two associative groups can, for example, be represented by formula (Ib) below:

Similarly, the compounds according to the invention comprising two groups Q, a "spacer" group and an associative group can, for example, be represented by formula (Ic) below:

According to the same principle, the compounds according to the invention comprising two groups Q, a "spacer" group and two associative groups can, for example, be represented by formula (Id) below:

Preferably, the associative group is chosen from an imidazolidinyl, ureyl, bis-ureyl, ureidopyrimidyl and triazolyl group.

Preferably, the group A corresponds to one of the formulae (II) to (VI) below:

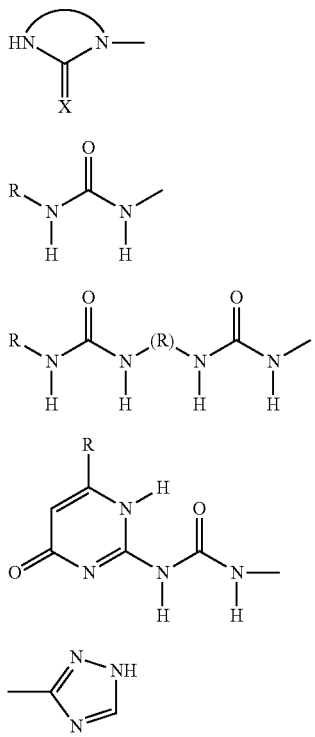

wherein:
R denotes a hydrocarbon-based group which can optionally contain heteroatoms,
X denotes an oxygen or sulfur atom, preferably an oxygen atom.

Preferably, the group A comprises a dinitrogenous or trinitrogenous heterocycle, generally containing 5 or 6 atoms, which is preferably dinitrogenous, and which comprises at least one carbonyl function. In at least one embodiment, the group A comprises an imidazolidinyl group of formula (II).

The group Q comprises an azodicarbonyl group preferably corresponding to the formula:

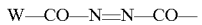

in which,
W represents
a group of formula:

in which:
—Z represents an oxygen or sulfur atom or an —NH or —NR' group,
—R' represents a $C_1$-$C_{20}$ alkyl group, preferably a $C_1$-$C_6$ alkyl, such as $C_1$-$C_4$ alkyl, including example methyl or ethyl,
or
a group of formula:

in which:
Sp', which may be identical to or different than Sp, is a divalent spacer group linking the azodicarbonyl functional group to another associative group A',
A', which may be identical to or different than A, is an associative group comprising at least one nitrogen atom,
A, Sp and Sp' possibly comprising one or more heteroatoms.

Preferably, the compounds which are subjects of the invention are represented by formula (VII)

in which
A is an associative group comprising at least one nitrogen atom,
Sp is a divalent spacer group linking the azodicarbonyl functional group to the associative group A,
W is as defined previously, and
A, Sp and Sp' can comprise one or more heteroatoms.

Compounds which are subjects of the invention are represented by formula (VIII) or (IX):

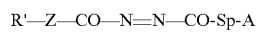

or

in which:
R', Z, Sp, A, Sp' and A' are as defined previously and A, Sp and Sp' can comprise one or more heteroatoms.

The "spacer" group Sp makes it possible to link at least one group Q and/or at least one associative group, and thus may be of any type known per se. However, the "spacer" group must interfere little, or not at all, with the groups Q and associative groups of the compound according to the invention.

Said "spacer" group is therefore considered to be a group that is inert with respect to the group Q, which preferably does not have any alkenyl functions capable of reacting with this group.

The "spacer" group is preferably a linear, branched or cyclic hydrocarbon-based chain, and can contain one or more aromatic radicals and/or one or more heteroatoms. Said chain can optionally be substituted, provided that the substituents are inert with respect to the groups Q.

According to one preferred embodiment, the "spacer" group is a linear or branched $C_1$-$C_{24}$, preferably $C_1$-$C_{10}$, alkyl chain, such as a linear $C_1$-$C_6$ alkyl chain, optionally comprising one or more heteroatoms chosen from nitrogen, sulfur, silicon or oxygen atoms.

In at least one embodiment, the "spacer" group Sp or Sp' is chosen from —$(CH_2)_y$—, —NH—$(CH_2)_y$— and —O—$(CH_2)_y$—, y being an integer from 1 to 6.

Preferably, the compound which is the subject of the invention is chosen from the compounds of formula (X) or (XI) below:

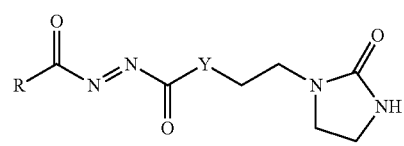

-continued

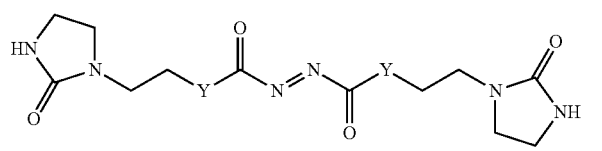
(XI)

in which:

Y represents a divalent group chosen from a methylene group, an oxygen atom, a sulfur atom and an —NH— group, and R represents a $C_1$-$C_6$ alkoxyl group, preferably a $C_1$-$C_4$ alkoxyl group, such as methoxyl or ethoxyl.

In at least one embodiment, the compound according to the invention can be chosen from the compounds of formulae (XII) to (XV) below:

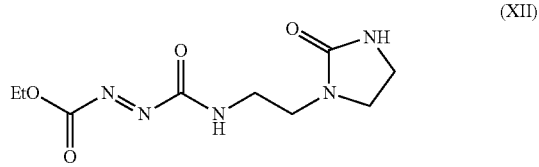
(XII)

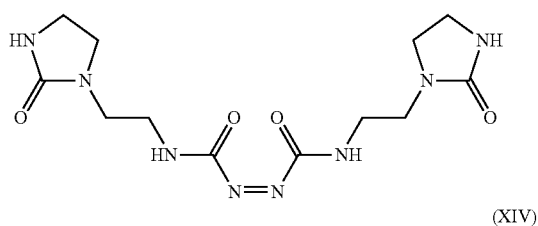
(XIII)

(XIV)

(XV)

The compounds which are subjects of the invention can be prepared in three steps according to the following general scheme:

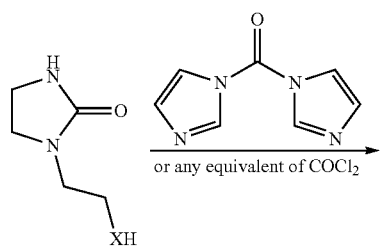

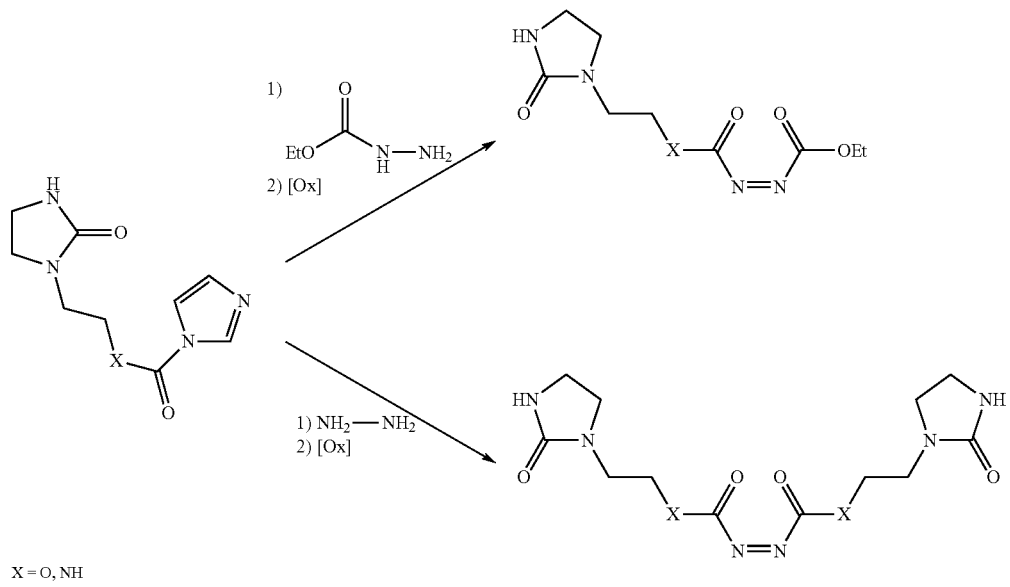

X = O, NH or else by direct reaction with a dialkyl azodicarboxylate or a dialkyl hydrazodicarboxylate according to the following reaction scheme:

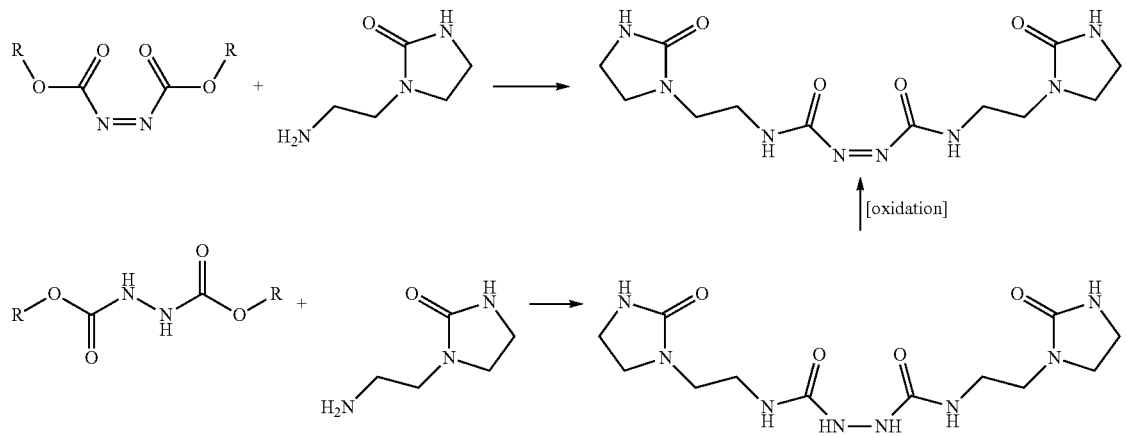

The following examples are provided by way of illustration, it being possible to envision other synthesis pathways or improvements to those described below.

Example 1

Preparation of (E)-ethyl 2-(2-(2-oxoimidazolidin-1-yl)ethylcarbamoyl)diazenecarboxylate

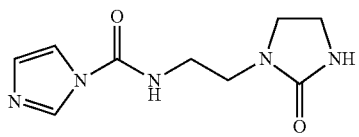 [SMILES: O=C1NCCN1CCNC(=O)n1ccnc1]

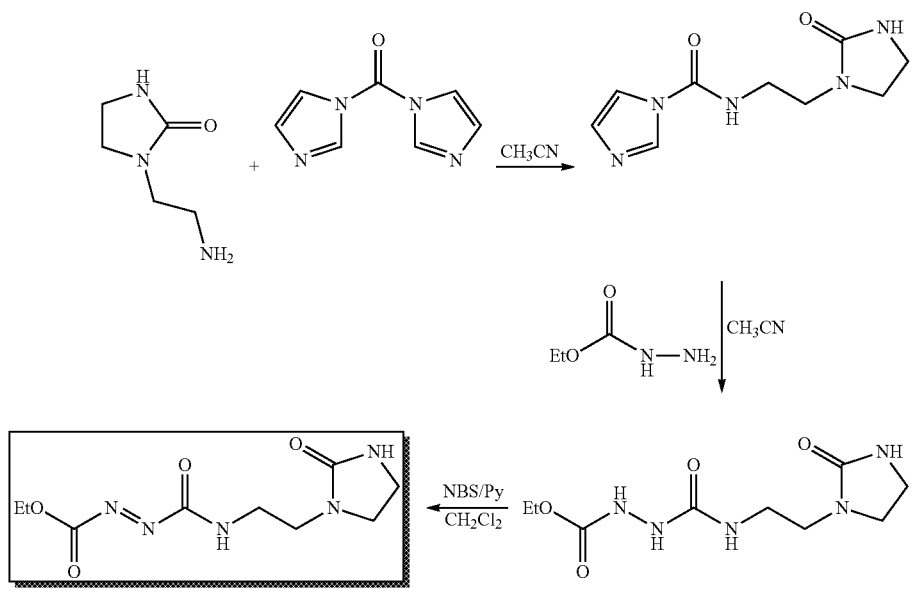

a) Preparation of N-(2-(2-oxoimidazolidin-1-yl)ethyl)-1H-imidazole-1-carboxamide The N-(2-(2-oxoimidazolidin-1-yl)ethyl)-1H-imidazole-1-carboxamide was prepared according to the following procedure:

Carbonyldiimidazole (64.2 g, 0.4 mol) was added, in one step, to a solution of 1-(2-aminoethyl)imidazolidin-2-one (46.5 g, 0.36 mol) in anhydrous acetonitrile (750 ml). The reaction medium was then stirred for 3 to 5 hours at ambient temperature. The precipitate obtained was filtered off and washed on the filter with dry acetonitrile (3 times 40 ml) and petroleum ether (twice 50 ml, 40/60° C. fraction) and, finally, dried for 10-15 hours at ambient temperature.

A white solid (74.5 g, yield 93%) with a melting point of 154° C. was obtained.

The molar purity was 88 mol % ($^1$H NMR).

$^1$H, $^{13}$C, $^{15}$N NMR characterization

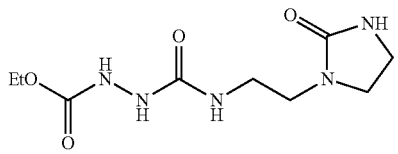 [SMILES: CCOC(=O)NNC(=O)NCCN1CCNC1=O]

| Atom | δ $^1$H (ppm) + mult. | δ $^{13}$C (ppm) | δ $^{15}$N (ppm) |
|---|---|---|---|
| 1 | — | 162.4 | — |
| 2 | 6.26 (s) | — | −302.7 ($^1J_{1H-15N}$ = 90 Hz) |
| 3 | 3.15 (t) | 37.5 | — |
| 4 | 3.34 (t) | 44.7 | — |
| 5 | — | — | −299.2 |
| 6 | 3.17 (t) | 42.5 | — |
| 7 | 3.28 (t) | 38.4 | — |
| 8 | 8.53 | — | −286.3 ($^1J_{1H-15N}$ = 90 Hz) |
| 9 | — | 148.8 | — |
| 10 | — | — | −185.1 |
| 11 | 8.14 (s) | 135.9 | — |
| 12 | — | — | −112.6 |
| 13 | 6.95 (s) | 139.5 | — |
| 14 | 7.57 (s) | 116.6 | — |

Solvent used: DMSO—calibration on the signal of DMSO at 2.44 ppm in $^1$H, 39.5 ppm in $^{13}$C and sr=19238.46 in $^{15}$N b) Preparation of ethyl 2-(2-(2-oxoimidazolidin-1-yl) ethylcarbamoyl)hydrazinecarboxylate

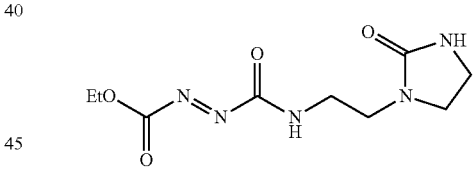

Ethyl hydrazinecarboxylate (38.0 g, 0.36 mol) was added, in one step, to N-(2-(2-oxoimidazolidin-1-yl)ethyl)-1H-imidazole-1-carboxamide (74.0 g, 0.33 mol, purity 88 mol % by NMR) in anhydrous acetonitrile (750 ml). The reaction medium was stirred for 3 hours at 70-75° C. and then for 2-3 hours at ambient temperature.

The precipitate was filtered off and washed with acetonitrile (twice 50 ml) and petroleum ether (twice 50 ml, 40/60° C. fraction) and, finally, dried for 10-15 hours at ambient temperature.

A white solid (79.6 g, yield 93%) with a melting point of 179° C. was obtained.

The molar purity was greater than 99% ($^1$H NMR).

$^1$H, $^{13}$C, $^{15}$N NMR characterization

| Atom | δ $^1$H (ppm) + mult. | δ $^{13}$C (ppm) | δ $^{15}$N (ppm) |
|---|---|---|---|
| 1 | — | 162.4 | — |
| 2 | 6.20 | — | −303.1 ($^1J_{1H-15N}$ = 90 Hz) |
| 3 | 3.13 (t) | 37.6 | — |
| 4 | 3.28 (t) | 45.0 | — |
| 5 | — | — | −298.2 |
| 6 | 2.99 (t) | 43.4 | — |
| 7 | 3.04 (t) | 37.9 | — |
| 8 | 6.33/7.69/8.30/8.68* | — | −301.3* |
| 9 | — | 158.3 | — |
| 10 | 6.33/7.69/8.30/8.68* | — | −301.3* |
| 11 | 6.33/7.69/8.30/8.68* | — | −301.3* |
| 12 | — | 156.9 | — |
| 13 | 3.96 (q) | 60.4 | — |
| 14 | 1.11 (t) | 14.6 | — |

Since protons 8, 10 and 11 are NH groups, their $^1$H chemical shift cannot be assigned precisely. The $^{13}$C chemical shift corresponds to group 8.

Solvent used: DMSO—calibration on the signal of DMSO at 2.44 ppm in $^1$H, 39.5 ppm in $^{13}$C and sr=19238.46 in 15N c) Preparation of ethyl 2-(2-(2-oxoimidazolidin-1-yl) ethylcarbamoyl)diazenecarboxylate, compound according to the invention N-Bromosuccinimide (6.87 g, 0.039 mol) in dichloromethane (100 ml) was added, in a single step, to a mixture of pyridine (3.05 g, 0.039 mol) and hydrazinecarboxylate (10.00 g, 0.039 mol) in dichloromethane (200 ml), cooled to 5-10° C. The reaction medium was stirred for 1 hour at 10° C. and then the organic phase was washed with water (twice 150 ml). The organic phase was then dried for 15 minutes over Na$_2$SO$_4$, and then the solvents were evaporated off under reduced pressure (T$_{bath}$ 18° C., 40-50 mbar). Diethyl ether (300 ml) was added and the reaction medium was stirred for 30-40 minutes at ambient temperature. The precipitate obtained was filtered off and washed on the filter with diethyl ether (3 times 40 ml) and, finally, dried for 10-15 hours at ambient temperature.

A yellow solid (6.95 g, yield 70%) with a melting point of 122° C. was obtained.

The molar purity was greater than 95% ($^1$H NMR).

A $^1$H, $^{13}$C NMR characterization is provided in the following table 1.

TABLE 1

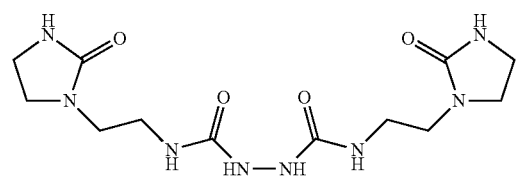 [SMILES: O=C(NCCN1CCNC1=O)NNC(=O)NCCN1CCNC1=O]

| Atom | δ ¹H (ppm) + mult. | δ ¹³C (ppm) |
|---|---|---|
| 1 | — | 162.20 |
| 2 | 6.27/9.12* | — |
| 3 | 3.15 (t) | 37.46 |
| 4 | 3.32 (t) | 44.59 |
| 5 | 3.17 (t) | 42.41 |
| 6 | 3.31 (t) | 38.44 |
| 7 | 6.227/9.12* | — |
| 8 | — | 160.42/161.25 |
| 9 | — | 160.42/161.25 |
| 10 | 4.41 (q) | 65.24 |
| 11 | 1.28 (t) | 13.83 |

Since protons 2 and 7 are NH groups, their $^1H$ chemical shift cannot be assigned precisely.

Solvent used: DMSO—calibration on the signal of DNSO at 2.44 ppm in $^1H$, 39.5 ppm in $^{13}C$

Example 2

Preparation of $N^1,N^2$-bis(2-(2-oxoimidazolidin-1-yl)ethyl)diazene-1,2-dicarboxamide in three steps from UDETA a) Preparation of $N^1,N^2$-bis(2-(2-oxoimidazolidin-1-yl)ethyl)hydrazine-1,2-dicarboxamide (SI-BIM-02)

Hydrazine hydrate (0.50 g, 0.01 mol) was added, in one step, to N-(2-(2-oxoimidazolidin-1-yl)ethyl)-1H-imidazole-1-carboxamide (4.46 g, 0.02 mol, purity 86 mol % by NMR) in anhydrous acetonitrile (100 ml) [product of example 1]. The reaction medium was stirred for 3 hours at 70-75° C. and then for 1-2 hours at ambient temperature. The precipitate was filtered off and washed with acetonitrile (25 ml) and petroleum ether (50 ml, 40/60° C. fraction) and, finally, dried for 10-15 hours at ambient temperature.

A white solid (3.16 g, 0.009 mol, yield 92%) with a melting point of 232° C. was obtained.

The molar purity was 900 ($^1H$ NMR).

A $^1H$ and $^{13}C$ NMR characterization in DMSO is provided in table 2 and in $D_2O$ is provided in table 3:

TABLE 2

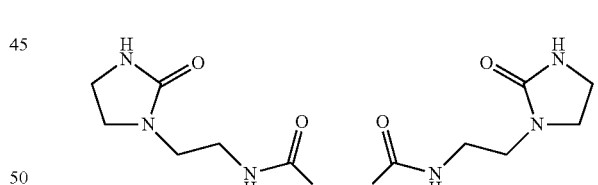

| Atom | δ ¹H (ppm) + mult. | δ ¹³C (ppm) |
|---|---|---|
| 1 | — | 162.3 |
| 2 | ~6.20 | — |
| 3 | 3.14 (t) | 37.5 |
| 4 | 3.29 (t) | 44.8 |
| 5 | 3.03 (t) | 43.2 |
| 6 | 3.03 (t) | 37.7 |
| 7 | ~6.31/7.56 | — |
| 8 | — | 158.6 |
| 9 | ~6.31/7.56 | — |

Solvent used: DMSO—calibration on the signal of DMSO at 2.44 ppm in $^1H$, 39.5 ppm in $^{13}C$

TABLE 3

| Atom | δ ¹H (ppm) + mult. | δ ¹³C (ppm) |
|---|---|---|
| 1 | — | 164.8 |
| 2 | — | — |
| 3 | 3.32 (t) | 38.0 |
| 4 | 3.47 (t) | 45.1 |
| 5 | 3.18 (t) | 42.9 |
| 6 | 3.25 (t) | 37.3 |
| 7 | — | — |
| 8 | — | 160.5 |
| 9 | — | — |

Solvent used: $D_2O$—calibration on the signal of water at 4.7 ppm in $^1H$, sr=0 in $^{13}C$.

b) Preparation of $N^1,N^2$-bis(2-(2-oxoimidazolidin-1-yl)ethyl)diazene-1,2-dicarboxamide, compound according to the invention N-Bromosuccinimide (0.534 g, 0.003 mol) was added, in one step, at ambient temperature, to a mixture of pyridine (0.237 g, 0.003 mol), $N^1,N^2$-bis(2-(2-oxoimidazolidin-1-yl)ethyl)hydrazine-1,2-dicarboxamide (1.03 g, 0.003 mol) and dichloromethane (50 ml). The reaction medium was stirred for 1 hour at ambient temperature. The precipitate was filtered off and washed on the filter with dichloromethane (10 ml) and dried for 1 hour. The precipitate was treated with water (20 ml) for 15 minutes, filtered and washed again with water (20 ml) and petroleum ether (20 ml) and, finally, dried for 10-15 hours at ambient temperature.

A light yellow solid (0.62 g, 0.002 mol, yield 61%) with a melting point of 208° C. (decomposition) was obtained.

The molar purity was 90% ($^1H$ NMR).

A $^1H$ and $^{13}C$ NMR characterization is provided in table 4.

TABLE 4

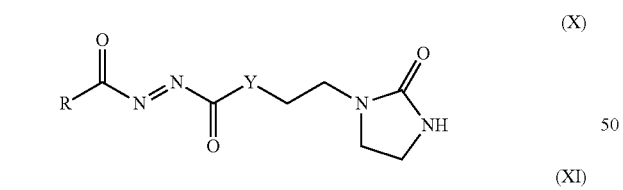

| Atom | δ $^1$H (ppm) + mult. | δ $^{13}$C (ppm) |
|------|----------------------|------------------|
| 1 | — | 162.3 |
| 2 | ~6.28/8.88 | — |
| 3 | 3.15 (t) | 37.5 |
| 4 | 3.32 (t) | 44.7 |
| 5 | 3.15 (t) | 42.6 |
| 6 | 3.28 (t) | 38.4 |
| 7 | ~6.28/8.88 | — |
| 8 | — | 161.7 |

Solvent used: DMSO—calibration on the signal of DMSO at 2.44 ppm in $^1$H, 39.5 ppm in $^{13}$C Example 3

Preparation of N$^1$,N$^2$-bis(2-(2-oxoimidazolidin-1-yl)ethyl)diazene-1,2-dicarboxamide in one step from UDETA 1-(2-Aminoethyl)imidazolidin-2-one (1.29 g, 0.010 mol) was added, in a single step, at ambient temperature, to a mixture of diisopropyl azo-1,2-dicarboxylate (1.01 g, 0.005 mol) in ethanol (20 ml). The reaction medium was stirred for one hour at ambient temperature. The precipitate was filtered off and washed with ethanol (20 ml), water (50 ml) and petroleum ether (20 ml), then dried for 10-15 hours at ambient temperature. A light yellow solid (1.26 g, 0.004 mol, yield 740) with a melting point of 193° C. (decomp.) was obtained. The purity by $^1$H NMR was 87 mol %.

The invention claimed is:

1. The compound represented by formula (X) or (XI) below:

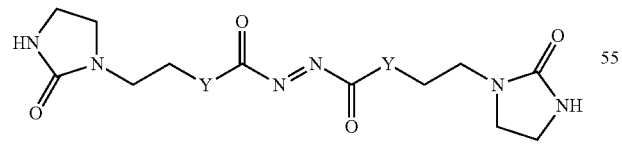

wherein:
Y represents a divalent group chosen from a methylene group, an oxygen atom, a sulfur atom, and an —NH— group; and
R represents a C$_1$-C$_5$ alkoxyl group.

2. The compound of claim 1, wherein R represents a C$_1$-C$_4$ alkoxyl group.

3. The compound of claim 1, wherein R represents a methyoxyl or ethoxyl group.

4. The compound chosen from the compounds of formulae (XII) to (XV) below:

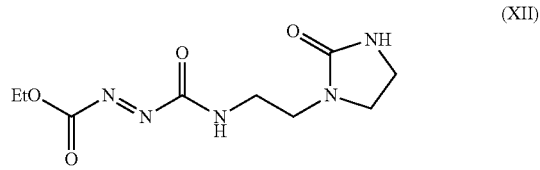

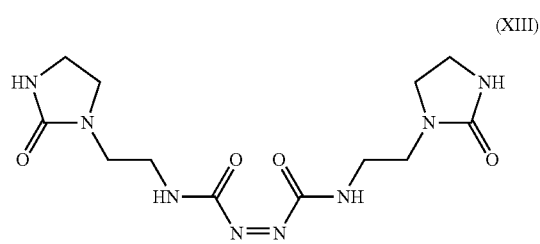

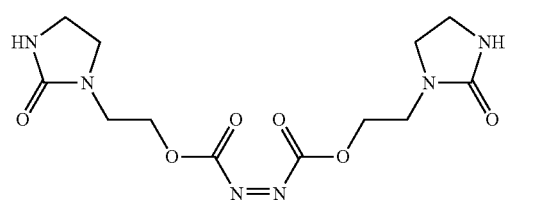

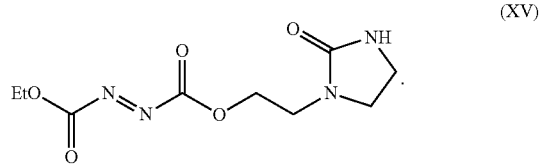

5. The compound represented by formula (X), (XI), (XII), (XIII), (XIV), or (XV) below:

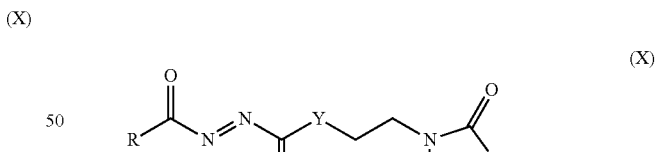

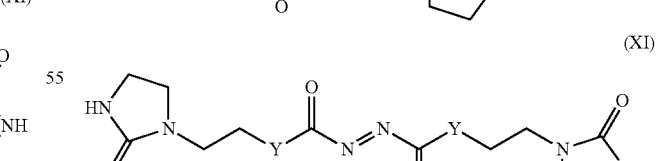

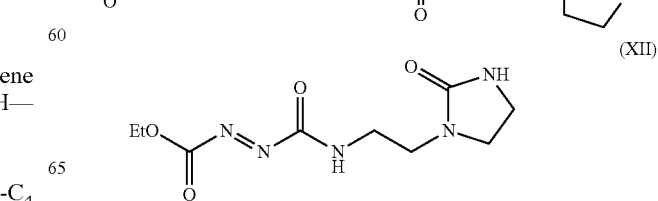

-continued
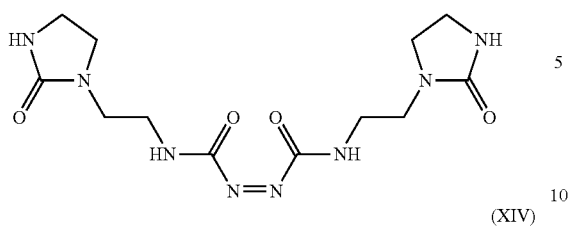
(XIII)
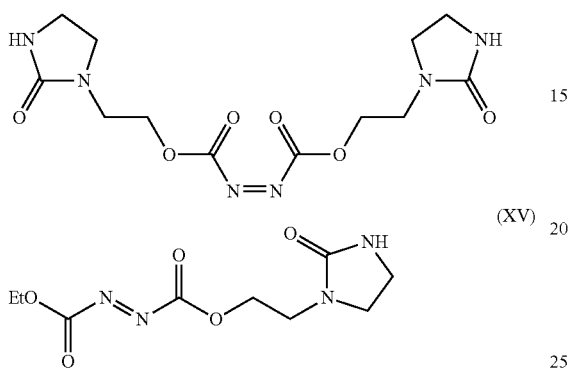
(XIV)
(XV)
wherein:
Y represents a divalent group chosen from a methylene group, an oxygen atom, a sulfur atom, and an —NH— group; and
R represents a $C_1$-$C_6$ alkoxyl group.
* * * * *